United States Patent
Metzner

(10) Patent No.: US 8,404,195 B2
(45) Date of Patent: Mar. 26, 2013

(54) RECEIVING AND TRANSFERRING STATION FOR COVERSLIPPED SPECIMEN SLIDES

(75) Inventor: Rolf Metzner, Überlingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1430 days.

(21) Appl. No.: 11/469,600

(22) Filed: Sep. 1, 2006

(65) Prior Publication Data

US 2008/0014119 A1    Jan. 17, 2008

(30) Foreign Application Priority Data

Sep. 5, 2005   (DE) .................. 10 2005 042 214

(51) Int. Cl.
*B01L 99/00*       (2010.01)
(52) U.S. Cl. .......... 422/537; 422/536; 422/50; 422/500; 422/501; 422/502; 436/180

(58) Field of Classification Search ............... 422/65–67, 422/99–100, 536–537, 50, 500–502; 436/180
See application file for complete search history.

(56) References Cited

U.S. PATENT DOCUMENTS

| | | | | |
|---|---|---|---|---|
| 5,209,903 | A * | 5/1993 | Kanamori et al. | 422/65 |
| 5,690,892 | A * | 11/1997 | Babler et al. | 422/63 |
| 6,430,309 | B1 * | 8/2002 | Pressman et al. | 382/133 |
| 6,821,072 | B2 | 11/2004 | Thiem et al. | |
| 2003/0049172 | A1 | 3/2003 | Thiem | |

* cited by examiner

*Primary Examiner* — Jyoti Nagpaul
(74) *Attorney, Agent, or Firm* — Hodgson Russ LLP

(57) ABSTRACT

A receiving and transferring station (1) for coverslipped specimen slides (2, 2', 2") comprises at least one vertically upright magazine frame (5), open toward the receiving side, for at least one specimen slide magazine (4) having horizontally oriented compartments (6), and a rotation apparatus, connected to the magazine frame (5) and having a vertically upright rotation axis, for conveying the magazine frame (5) from a receiving position (3) into a transferring position (8).

1 Claim, 2 Drawing Sheets

RECEIVING AND TRANSFERRING STATION FOR COVERSLIPPED SPECIMEN SLIDES

CROSS REFERENCE TO RELATED APPLICATIONS

This application claims priority of German patent application no. 10 2005 042 214.4 filed Sep. 5, 2005, which is incorporated by reference herein.

FIELD OF THE INVENTION

The invention relates to a receiving and transferring station for coverslipped specimen slides.

BACKGROUND OF THE INVENTION

In clinical laboratories or pharmaceutical companies and at research service provider facilities, a large number of different samples are processed every day and prepared for histological investigations by scientists, physicians, and pathologists. The usual procedure is to take the sample from the patient, embed the sample in, for example, paraffin, and then cut it into thin sections using microtomes.

The thin sections are, as a rule, placed onto specimen slides and covered with a thin glass or plastic plate for protection from environmental influences. To enhance diagnosis capabilities, the samples are often stained with different staining techniques before coverslipping.

In order to meet ever more stringent requirements in clinical and pathological histology and cytology, and to maintain competitiveness despite enormous time and cost pressure, many activities previously performed manually by laboratory personnel are being streamlined with the aid of automatic equipment.

For example, so-called stainers (automatic staining machines) have become known for staining the samples. Coverslipping of the specimen slides is facilitated by coverslipping machines.

It is known from DE 101 44 042 A1 and DE 101 44 989 A1 to connect a stainer, via a transfer module, to a coverslipping machine and to transport stained sections automatically for coverslipping. In this fashion, a large number of coverslipped samples are produced at short time intervals and are made available, at the output end of the system, for further investigation.

Subsequent investigation of the samples by physicians, scientists, and pathologists requires substantially more time, however, and also occurs more irregularly than the production of coverslipped samples on specimen slides using the system described above. Even automatically operating digital scanning devices, which convert the samples into high-resolution "digital slides," take between two and 20 minutes to scan a specimen slide, depending on the size of the specimen. It is common to have a backup of finished coverslipped specimen slides at the output end of the coverslipping machine.

SUMMARY OF THE INVENTION

The object of the invention is to simplify and maximally automate handling, over the entire evaluation process, of specimen slides for histology. The intention is to automate the transfer of stained and coverslipped specimen slides to a downstream digital specimen slide scanner system, and to absorb any possible backup resulting from different processing times prior to scanning.

This object is achieved, according to the present invention, by a receiving and transferring station for coverslipped specimen slides that contains at least one vertically upright magazine frame, open toward the receiving side, for at least one specimen slide magazine having horizontally oriented compartments, and a rotation apparatus, connected to the magazine frame and having a vertically upright rotation axis, for conveying the magazine frame from a receiving position into a transferring position.

For vertical shifting and easy filling of the compartments in the specimen slide magazines, the magazine frame comprises a transport device for vertical displacement of the specimen slide magazines. In this fashion, the individual compartments of the specimen slide magazines can be brought progressively into the receiving position. In an alternative embodiment, a transport apparatus for vertical displacement is located in the lower housing region of the receiving and transferring station, and introduces the specimen slide magazines from below into the magazine frames.

The invention is distinguished by the fact that the height of the magazine frame is provided for the reception two specimen slide magazines, thereby increasing the receiving capacity.

For easy filling of the magazine frame with empty specimen slide magazines, the latter are insertable from above into the magazine frame. Filled specimen slide magazines are of course also removable from above in this fashion.

If the rotation apparatus contains a turntable on whose periphery multiple magazine frames are mounted, the receiving and transferring station can receive a plurality of specimen slides. If six magazine frames are arranged evenly on the periphery of the turntable, rotational control of the apparatus can be configured in particularly simple fashion.

In a further embodiment of the invention, there is arranged above the turntable, at a location intersected by the rotation axis, a stationary ejection apparatus whose ejection arms are shiftable in the direction of the transferring position in a compartment plane, in order to transfer individual specimen slides to the next processing apparatus. With a particular embodiment of the ejection apparatus, however, it is also possible to convey a magazine either vertically upward or downward out of the magazine frame, and thus transfer the magazine as a unit.

An electronically controllable rotation apparatus makes it possible, in the context of the receiving and transferring station according to the present invention, on the one hand to position magazine frames having empty specimen slide magazines in the receiving region in specific fashion. On the other hand, the possibility exists of delivering magazine frames having filled specimen slide magazines to the transfer position, and ejecting the specimen slides there.

For that purpose, the ejection apparatus is advantageously likewise embodied in electronically controllable fashion.

With an electronically controllable embodiment of the transport device for vertical displacement, the procedure of sliding specimen slides into the compartments of the specimen slide magazines can be synchronized and optimized interactively with the ejection apparatus and the rotation apparatus.

In particularly advantageous fashion, the receiving position of the receiving and transferring station for coverslipped specimen slides is associated with the output side of a coverslipping machine. Cyclical introduction of the specimen slides produced in the coverslipping machine into compartments of the specimen slide magazines takes place with no further intervening manual step.

For easy filling of the specimen slide magazines, the magazines are lowerable within the magazine frame in the receiving position. This makes it easy to adapt to existing coverslipping machines, which comprise at their output side only a horizontal shifting (dispensing) of the coverslipped specimen slides. Further possibilities for introducing specimen slides into the receiving and transferring station according to the present invention are, of course, not intended to be excluded from protection. For example, with an appropriate configuration of the substructure of the apparatus in the receiving position, it is also possible to push empty specimen slide magazines under the magazine frames and insert them from below into the magazine frames. With this filling method, as soon as the lowest compartment of a specimen slide magazine is filled with a coverslipped specimen slide, the specimen slide magazines can be secured in the magazine frame to prevent them from slipping out, and the rotation apparatus can deliver the next empty magazine frame to the receiving position.

In a further embodiment of the invention, the transferring position of the receiving and transferring station is associated with a digital scanning device for producing so-called digital slides. This makes possible, especially in coaction with the electronically controllable ejection apparatus, a controlled automatic transfer of specimen slides. If the scanning operation requires more time because of the size of the sample, it is possible to link the control system of the receiving and transferring station to that of the scanning device, and allow the latter to generate the instruction to transfer the next specimen slide to be scanned. Operation in terms of receiving specimen slides can otherwise continue without interference during a scanning procedure, until the supply of empty compartments in the receiving and transferring station has been exhausted. The transfer of specimen slides to the scanning device can proceed autarchically with no supervision by operating personnel, including at night. A backup that has occurred as a result of the rapid (as compared with the scanning operation) reception of coverslipped specimen slides can be cleared in this fashion.

The invention is further distinguished by the fact that the receiving position and the transferring position can be arranged with a 180-degree offset from one another. This makes possible an ergonomic and space-saving configuration of a system made up of a coverslipping machine, receiving and transferring station, and digital scanning device arranged next to one another.

BRIEF DESCRIPTION OF THE DRAWINGS

The invention will be described and explained in more detail below with reference to an exemplifying embodiment depicted schematically in the drawings, in which.

DETAILED DESCRIPTION OF THE INVENTION

Figure 1:
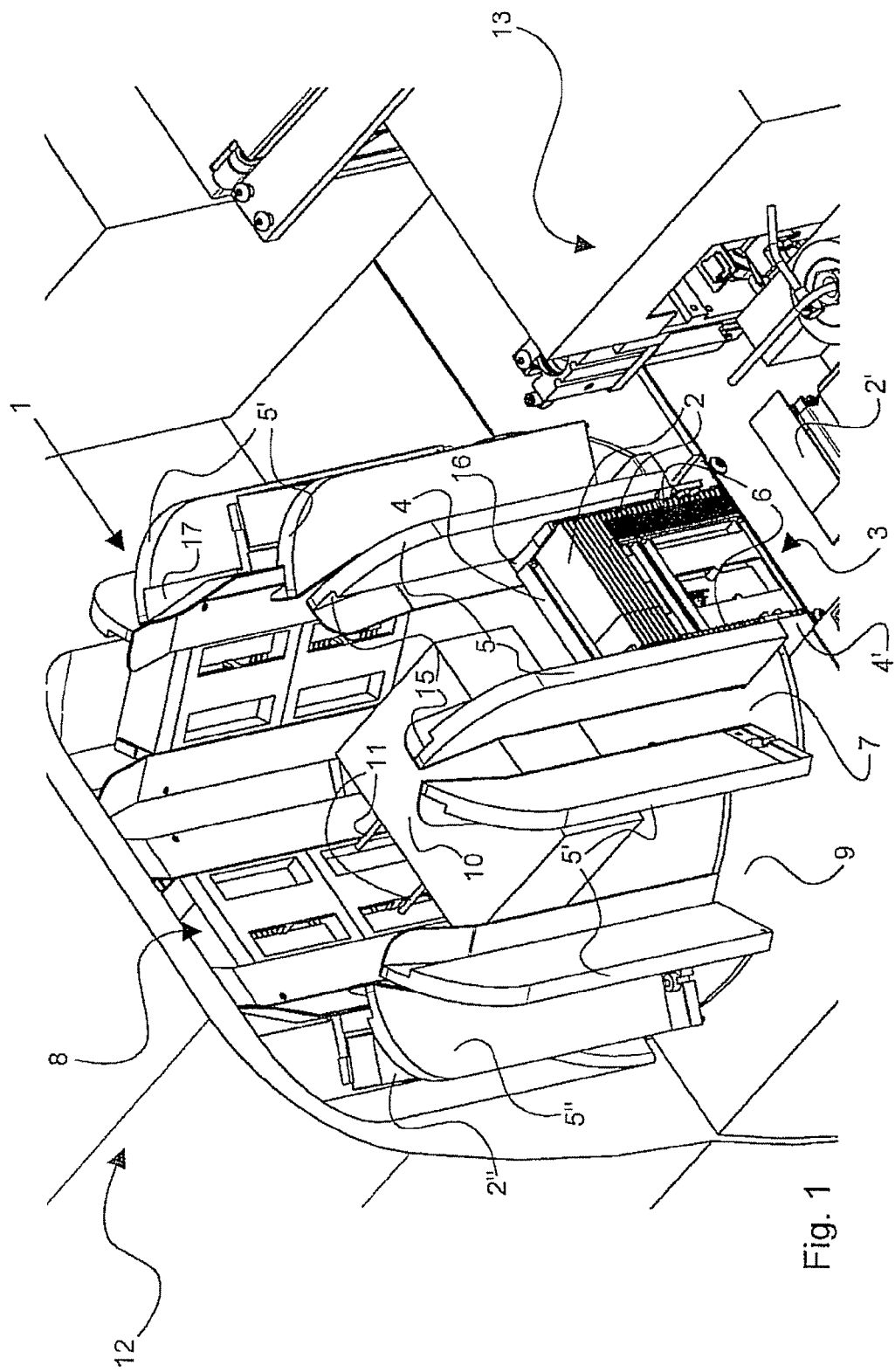
FIG. 1 shows a receiving and transferring station viewed obliquely from above.

FIG. 1 shows a receiving and transferring station 1 for coverslipped specimen slides 2, 2', 2", in which station a specimen slide magazine 4, located in a receiving position 3, is depicted in a lowered position. Specimen slide magazine 4 is inserted in vertically shiftable fashion in a magazine frame 5. Coverslipped specimen slides 2 are located in the horizontally oriented compartments 6. Specimen slide magazine 4 is vertically shifted, by a transport device (not depicted further) for vertical displacement of compartments 6, until an open compartment 6 can be filled with a coverslipped specimen slide 2'. Projecting out in the lower region of magazine frame 5 is a second, empty specimen slide magazine 4' that, for the reception of further specimen slides 2', is inserted upward into magazine frame 5 via the transport device for vertical adjustment. As soon as specimen slide magazine 4' is also filled with specimen slides 2, 2', specimen slide magazines 4, 4' are secured by way of a locking mechanism (not depicted further) to prevent magazine frames 5, 5', 5" from slipping or falling out.

Magazine frames 5, 5', 5" comprise, in the rear region, vertically extending guide grooves 15. In the base region of specimen slide magazines 4, 4', shaped-on lateral ridges 16 engage into guide grooves 15. Specimen slide magazines 4, 4' are thereby guided vertically in magazine frames 5, 5', 5". For easy manual insertion of specimen slide magazines 4, 4' into magazine frames 5, 5', 5", guide grooves 15 comprise a widened groove cross section 17 in the upper region.

A rotation apparatus performs a rotary motion, thereby causing magazine frame 5 to be moved toward transferring position 8. On the periphery of the rotation apparatus, which is embodied as a turntable 7, multiple magazine frames 5, 5', 5" having recesses 9 are arranged in the base region of magazine frames 5, 5'. As a result of the rotary motion, magazine frame 5" having specimen slides 2" is delivered to transferring position 8. At transferring position 8 specimen slides 2" are transferred, by an ejection apparatus 10 having ejection arms 11, to a digital scanning device 12 depicted schematically in FIG. 1.

Figure 2:
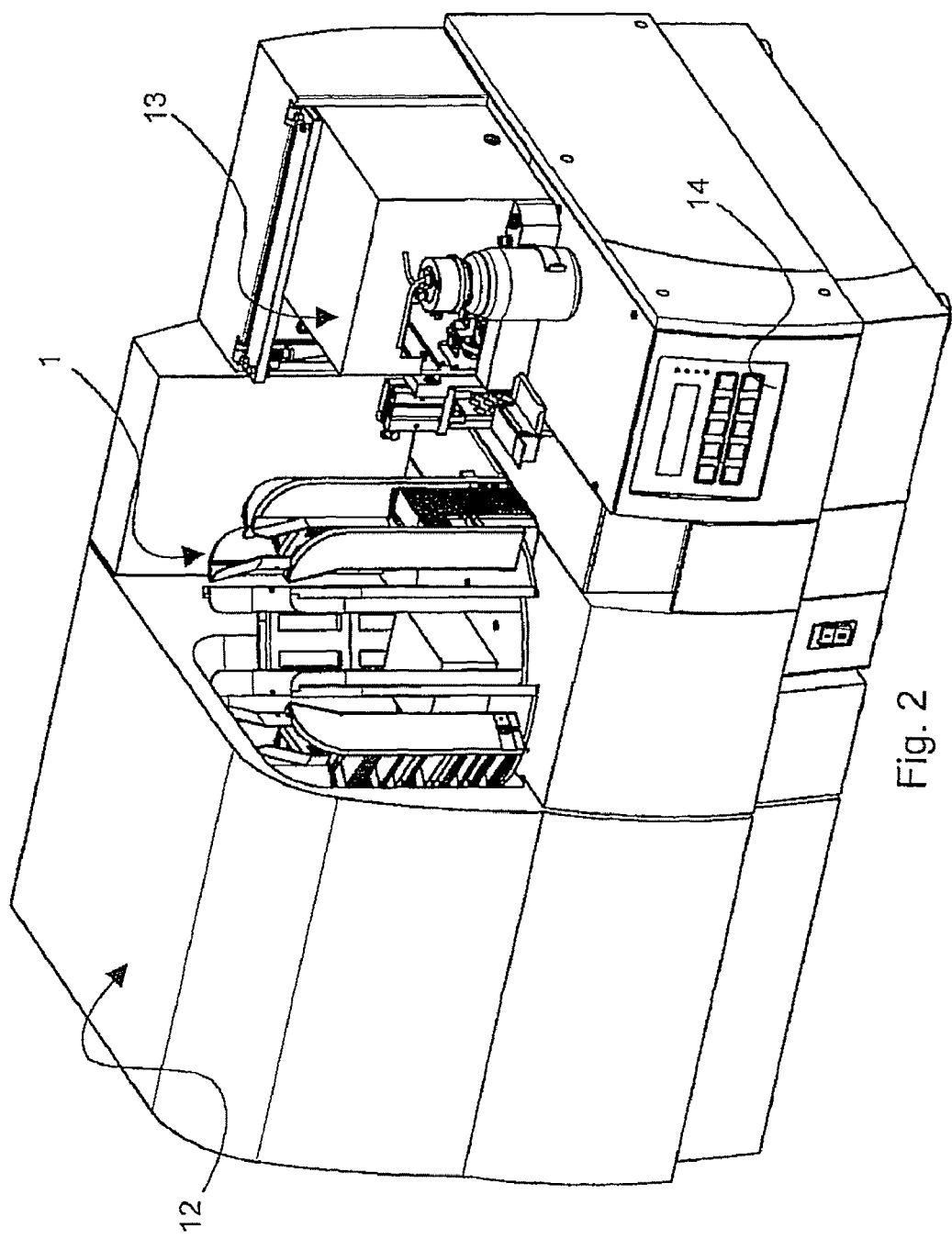
FIG. 2 shows a receiving and transferring station in an arrangement between a coverslipping machine and a digital scanning device.

FIG. 2 is an overall view of a system made up of a coverslipping machine 13, receiving and transferring station 1 that is described more thoroughly in FIG. 1, and a digital scanning device 12. All the controllable apparatuses can be monitored and programmed via a control panel 14 of an electronic control device.

Codes, with which an allocation of the sample to a patient record and sample record in a database system can be performed, are advantageously applied onto the specimen slides 2, 2', 2". A code applied onto the specimen slide magazine 4, 4' makes possible, together with a stored compartment number, a determination of the exact introduction position of a specimen slide even after a specimen slide magazine has been removed from the receiving and transferring station. Specific recovery of individual samples from a plurality of samples is facilitated. This makes possible, in coaction with the electronic control systems of the receiving and transferring station, a variety of automatic working sequences. For example, the samples can be transferred to the downstream digital scanning device 12 in almost any desired sequence. Prioritized samples can be handled preferentially with no need to wait for the processing of previously introduced specimen slides. The possibility also exists of delivering further specimen slides to the specimen slide magazines in the receiving region during the scanning operation. The reception of further specimen slides can be briefly interrupted in order to return a sample that has just been scanned, without creating a backup in the coverslipping machine 13. It is likewise possible first to scan all the samples that have a short scanning time, in order to gain rapid access to a plurality of scanning results. The processing of specimen slides having samples with a longer scanning time can be postponed in order to process them later, for example at night without supervision. In the case of a sequential processing of the samples in the order in which they were introduced into the specimen slide magazines (FIFO principle), the possibility exists of transferring scanned specimen slides to a storage system downstream from the digital scanning device. As a result, empty specimen slide magazines are constantly leaving the transferring position, and empty specimen slide magazines are constantly being delivered to the receiving region. If there is no storage system placed downstream from the scanning device, and if the specimen slides must therefore be introduced back into the specimen slide magazine at the same position after scanning of the sample is complete, filled specimen slide magazines can be removed from the receiving and transferring station after leaving the transferring position. On the basis of the code on the specimen slide and on the specimen slide magazines, and information from the database system, specific access to individual samples is possible at any later time.

Parts List

1 Receiving and transferring station for coverslipped specimen slides
2, 2', 2" Specimen slides
3 Receiving position
4, 4' Specimen slide magazine
5, 5', 5" Magazine frames
6 Compartment
7 Turntable
8 Transferring position
9 Recesses
10 Ejection apparatus
11 Ejection arms
12 Digital scanning device
13 Coverslipping machine
14 Control panel
15 Guide groove
16 Ridges
17 Widened groove cross section

What is claimed is:

1. A system comprising:
 a coverslipping machine having an output station to which coverslipped specimen slides are delivered by the coverslipping machine;
 a digital scanning device having an input station from which specimen slides are selected for scanning;
 a receiving and transferring station located between the coverslipping machine and the digital scanning device, the receiving and transferring station automatically receiving the coverslipped specimen slides from the output station of the coverslipping machine and transferring the coverslipped specimen slides to the input station of the digital scanning device, wherein the receiving and transferring station comprises:
  at least one specimen slide magazine having horizontally oriented compartments;
  at least one vertically upright magazine frame configured to receive the at least one specimen slide magazine, the magazine frame having an open side through which specimen slides are inserted into the compartments of the at least one specimen slide magazine and the magazine frame being configured such that a specimen slide magazine received by the magazine frame is guided for vertical displacement relative to the magazine frame;
  a transport apparatus for vertical displacement arranged in a lower housing region of the receiving and transferring station to introduce empty specimen slide magazines from below into the magazine frame;
  a rotation apparatus connected to the magazine frame and having a vertically upright rotation axis about which the rotation apparatus rotates, the rotation apparatus conveying the magazine frame from a receiving position to a transferring position; and
  an ejection apparatus located above the rotation apparatus, the ejection apparatus having at least one ejection arm shiftable to push a specimen slide out of the specimen slide magazine held by the magazine frame in the transferring position and into the input station of the digital scanning device.

\* \* \* \* \*